United States Patent [19]

Tidwell et al.

[11] Patent Number: 5,668,166

[45] Date of Patent: Sep. 16, 1997

[54] METHODS OF INHIBITING PNEUMOCYSTIS CARINII PNEUMONIA AND COMPOUNDS USEFUL THEREFOR

[75] Inventors: Richard R. Tidwell, Pittsboro; James E. Hall, Chapel Hill, both of N.C.; David W. Boykin, Atlanta, Ga.

[73] Assignees: Georgia State University Research Foundation, Inc., Atlanta, Ga.; The University of North Carolina at Chapel Hill, Chapel Hill, N.C.

[21] Appl. No.: 474,440

[22] Filed: Jun. 7, 1995

[51] Int. Cl.$^6$ .................................................. A61K 31/40
[52] U.S. Cl. ................................................... 514/411
[58] Field of Search ........................................ 514/411

[56] References Cited

U.S. PATENT DOCUMENTS 4,933,347  6/1990  Tidwell et al. .......................... 514/256
4,963,589  10/1990 Tidwell et al. .......................... 514/636

OTHER PUBLICATIONS

Ram et al 118 CA: 254855t 1993.
Randelia et al 97 CA: 35933m 1982.
Shukla et al 121 CA: 255584c 1994.
Edman et al 109 CA: 125671v 1988.
S. Jones et al.; Novel Pentamidine Analogs in the Treatment of Experimental Pneumocystis Carinii Pneumonia. *Antimicrob. Agents Chemother.* 34: 1026–1030 (1990).
B. Berger et al.; Metabolic N–Hydroxylation of Pentamidine In Vitro. *Antimicrob. Agents Chemother.* 34: 1678–1684 (1990).
R. Tidwell et al.; Analogues of 1,5–Bis(4–amidinophenoxy)pentane (Pentamidine) in the Treatment of Experimental Pneumocystis carinii Pneumonia. *J. Med. Chem* 33:1252–1257 (1990).
I. Donkor et al.; Pentamidine Congeners. 2. 2-Butene–Bridged Aromatic Diamidines and Diimidazolines as Potential Anti–Pneumocystis carinii Pneumonia Agents. *J. Med. Chem.* 37:4554–4557 (1994).
M.Cory et al.; Structure and DNA Binding Activity of Analogues of 1,5–Bis(4–amidinophenoxy)pentane (Pentamidine). *J. Med. Chem.* 35:431–438 (1992).
Ram et al.; Chemotheraputic agents. XXV. Synthesis and leichmanicidal activity of carbazolylpyrimidines, *Chemical Abstracts*, 118, No. 25, p. 878, col. 2, abst. #254855t, *Eur J Med Chem* 27(8):851–5 (21 Jun. 1993).
Bassin et al.; Chlorosulfonation of some polynuclear heterocyclic compounds, *Chemical Abstracts*, 118, No. 25, p. 854, col. 1–2, abst. #254658f, *Phosphorus, Sulfur, Silicon Relat. Elem.*, 72(1–4), pp. 157–170 (21 Jun. 1993).
PCT Search Report for PCT/US96/08464. 1996.

*Primary Examiner*—Russell Travers
*Attorney, Agent, or Firm*—Bell, Seltzer, Park & Gibson, P.A.

[57] ABSTRACT

The present invention provides methods for treating *Pneumocystis carinii* pneumonia. The method comprises administering to the subject a compound of Formula I:

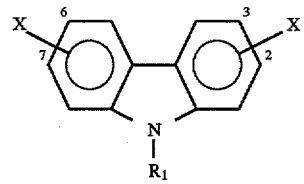

wherein:

X is located in the para or meta positions and is loweralkyl, loweralkoxy, alkoxyalkyl, hydroxyalkyl, aminoalkyl, alkylaminoalkyl, cycloalkyl, aryl, alkylaryl, halogen, or

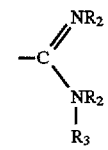

wherein:

each $R_2$ is independently selected from the group consisting of H, loweralkyl, alkoxyalkyl, hydroxyalkyl, aminoalkyl, alkylaminoalkyl, cycloalkyl, aryl, or alkylaryl or two $R_2$ groups together represent $C_2$–$C_{10}$ alkylene, or two $R_2$ groups together represent

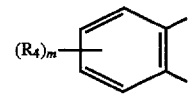

wherein
m is from 1–3 and $R_4$ is H,

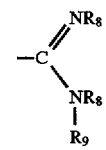

or —$CONHR_5NR_6R_7$, wherein $R_5$ is loweralkyl, $R_6$ and $R_7$ are each independently selected from the group consisting of H and lower alkyl; each $R_8$ is independently selected from the group consisting of H, loweralkyl, alkoxyalkyl, hydroxyalkyl, aminoalkyl, alkylaminoalkyl, cycloalkyl, aryl, or alkylaryl, or two $R_8$ groups together represent $C_2$–$C_{10}$ alkylene; $R_9$ is H, hydroxy, loweralkyl, alkoxyalkyl, hydroxyalkyl, aminoalkyl, alkylaminoalkyl, cycloalkyl, aryl, or alkylaryl;

$R_3$ is H, hydroxy, loweralkyl, alkoxyalkyl, hydroxyalkyl, aminoalkyl, alkylaminoalkyl, cycloalkyl, aryl, or alkylaryl;

$R_1$ is H, loweralkyl, alkoxyalkyl, hydroxyalkyl, aminoalkyl, alkylaminoalkyl, cycloalkyl, aryl, alkylaryl, or halogen; or a pharmaceutically acceptable salt thereof.

7 Claims, No Drawings

METHODS OF INHIBITING *PNEUMOCYSTIS CARINII* PNEUMONIA AND COMPOUNDS USEFUL THEREFOR

The present invention was made with Government support under Grant Number 5-UO1-AI33363-03 from the National Institutes of Health. The Government has certain rights to this invention.

FIELD OF THE INVENTION

The present invention relates to methods useful in combating *Pneumocystis carinii* pneumonia and compounds useful therefor.

BACKGROUND OF THE INVENTION

Pentamidine is used for the treatment of *Pneumocystis carinii* pneumonia, or "PCP". The importance of pentamidine has dramatically escalated recently due to the marked increase of patients suffering from PCP. The increase in the afflicted patient population is an unfortunate consequence of the increasing presence of the Acquired Immunodeficiency Syndrome ("AIDS"). It is now estimated that approximately 70 percent of AIDS patients contract PCP. Because of the high incidence of PCP in AIDS patients, pentamidine has found utility not only in the treatment of PCP, but also as prophylaxis, in preventing or delaying the initial onset or recurrence of PCP, especially in AIDS patients. Currently, pentamidine is most commonly administered as a therapeutic agent by intravenous infusion and as a prophylactic agent by aerosol dosage.

However, an unfortunate side effect of pentamidine is its toxicity. Some fatalities have been attributed to severe hypotension, hypoglycemia, and cardiac arrhythmias in patients treated with pentamidine. Contrawise, insufficient dosage may result in dissemination of disease beyond the lung, an occurrence which is associated with a poor prognosis.

Pentamidine is presently in limited use because of cost and toxicity. Therapeutic drug monitoring is not used because of the cost and complexity of the currently available assay techniques which require the extraction of plasma and High Performance Liquid Chromatography analysis. As a result, the toxicity of pentamidine is a significant concern, which is driving the market toward the development of pentamidine substitutes capable of avoiding or minimizing the undesirable side effects associated with the use of pentamidine. Accordingly, it is an object of the present invention to provide new compounds useful in the treatment of *P. carinii* pneumonia.

SUMMARY OF THE INVENTION

As a first aspect, the present invention provides a method of treating *P. carinii* pneumonia. The method includes administering to a subject in need of such treatment an amount effective to treat *P. carinii* pneumonia a compound of Formula I:

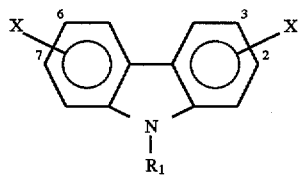

wherein:
X is located in the para or meta positions and is loweralkyl, loweralkoxy, alkoxyalkyl, hydroxyalkyl, aminoalkyl, alkylaminoalkyl, cycloalkyl, aryl, alkylaryl, halogen, or

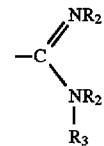

wherein:
each $R_2$ is independently selected from the group consisting of H, loweralkyl, alkoxyalkyl, hydroxyalkyl, aminoalkyl, alkylaminoalkyl, cycloalkyl, aryl, or alkylaryl or two $R_2$ groups together represent $C_2$–$C_{10}$ alkylene, or two $R_2$ groups together represent

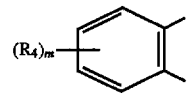

wherein
m is from 1–3 and $R_4$ is H,

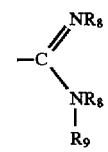

or —CONHR$_5$NR$_6$R$_7$, wherein $R_5$ is loweralkyl, $R_6$ and $R_7$ are each independently selected from the group consisting of H and lower alkyl; each $R_8$ is independently selected from the group consisting of H, loweralkyl, alkoxyalkyl, hydroxyalkyl, aminoalkyl, alkylaminoalkyl, cycloalkyl, aryl, or alkylaryl, or two $R_8$ groups together represent $C_2$–$C_{10}$ alkylene; $R_9$ is H, hydroxy, loweralkyl, alkoxyalkyl, hydroxyalkyl, aminoalkyl, alkylaminoalkyl, cycloalkyl, aryl, or alkylaryl;

$R_3$ is H, hydroxy, loweralkyl, alkoxyalkyl, hydroxyalkyl, aminoalkyl, alkylaminoalkyl, cycloalkyl, aryl, or alkylaryl;

$R_1$ is H, loweralkyl, alkoxyalkyl, hydroxyalkyl, aminoalkyl, alkylaminoalkyl, cycloalkyl, aryl, alkylaryl, or halogen; or a pharmaceutically acceptable salt thereof.

As a second aspect, the present invention provides compounds useful for the treatment of *P. carinii* pneumonia. The compounds have the structural Formula (I), described above. Currently preferred compounds of Formula I include, but are not limited to, 2,7-Diamidinocarbazole dihydrochloride, 3,6-Diisopropylamidinocarbazole dihydrochloride, 3,6-Bis (2-imidazolinyl)-9-methylcarbazole dihydrochloride, 3,6-Bis[1,4,5,6-tetrahydropyrimidinyl)]-9-methylcarbazole dihydrochloride, and pharmaceutically acceptable salts thereof.

As a third aspect, the present invention provides a method of treating *Cryptococcus neoformans* in a patient in need of such treatment. The method includes administering to a patient in need of such treatment, a compound of Formula I above, in an amount effective to treat *C. neoformans*. Novel compounds useful for treating *C. neoformans* are also disclosed.

As a fourth aspect, the present invention provides a method of treating *Cryptosporidium parvum* in a patient in need of such treatment. The method includes administering to a patient in need of such treatment, a compound of Formula I above, in an amount effective to treat *C. parvum*. Novel compounds useful for treating *C. parvum* are also disclosed.

As a fifth aspect, the present invention provides a method of treating *Candida albicans* in a patient in need of such treatment. The method includes administering to a patient in need of such treatment, a compound of Formula I above, in an amount effective to treat *C. albicans*. Novel compounds useful for treating *C. albicans* are also disclosed.

The foregoing and other objects and aspects of the present invention are explained in detail in the specification set forth hereinbelow.

DETAILED DESCRIPTION OF THE INVENTION

As used herein, the term "lower alkyl," refers to C1 to C4 linear or branched alkyl, such as methyl, ethyl, propyl, butyl, isopropyl, sec-butyl, and tert-butyl. Methyl is currently preferred. The term "cycloalkyl" as used herein refers to C3 to C6 cyclic alkyl, such as cyclopropyl, cyclobutyl, cyclopentyl, and cyclohexyl. Cyclohexyl is currently preferred. The term "aryl" as used herein refers to C3 to C10 cyclic aromatic groups such as phenyl, naphthyl, and the like, and includes substituted aryl groups such as tolyl. The term "hydroxyalkyl" as used herein refers to C1 to C4 linear or branched hydroxy-substituted alkyl, i.e., —CH$_2$OH, —(CH$_2$)$_2$OH, etc. The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc. The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

As noted above, the methods of the present invention are useful for treating *P. carinii* pneumonia, and infections caused by *C. neoformans*, *C. parvum*, and *C. albicans*. The methods of the present invention are useful for treating these conditions in that they inhibit the onset, growth, or spread of the condition, cause regression of the condition, cure the condition, or otherwise improve the general well-being of a subject inflicted with, or at risk of contracting the condition.

Subjects to be treated by the methods of the present invention are typically human subjects although the methods of the present invention may be useful with any suitable subject known to those skilled in the art.

As noted above, the present invention provides pharmaceutical formulations comprising the aforementioned compounds of Formula I, or pharmaceutically acceptable salts thereof, in pharmaceutically acceptable carriers for aerosol, oral, and parenteral administration as discussed in greater detail below. Also, the present invention provides such new compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration. The duration of the treatment is usually once per day for a period of two to three weeks or until the *P. carinii* pneumonia is essentially controlled. Lower doses given less frequently can be used to prevent or reduce the incidence of recurrence of the infection.

In accordance with the present method, a compound of Formula I, or a pharmaceutically acceptable salt thereof, may be administered orally or through inhalation as a solid, or may be administered intramuscularly or intravenously as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

Besides providing a method for treating *P. carinii* pneumonia, the compounds of Formula I also provide a method for prophylaxis against *P. carinii* pneumonia in an immunocompromised patient, such as one suffering from AIDS, who has had at least one episode of *P. carinii* pneumonia, but who at the time of treatment is not exhibiting signs of pneumonia. As *P. carinii* pneumonia is an especially potentially devastating disease for immunocompromised patients it is preferable to avoid the onset of *P. carinii* pneumonia, as compared to treating the disease after it has become symptomatic. Accordingly, the present invention provides a method for the prophylaxis against *P. carinii* pneumonia comprising administering to the patient a prophylactically effective amount of a compound of Formula I or a pharmaceutically acceptable salt thereof. The forms for administration of the compound or salt in accordance with this method may be the same as utilized for the purpose of actually treating a patient suffering from *P. carinii* pneumonia.

An additional useful aspect of the present invention is a method for prophylaxis against even an initial episode of *P. carinii* pneumonia in an immunocompromised patient who has never experienced an episode of *P. carinii* pneumonia. In this respect, a patient who has been diagnosed as being immunocompromised, such as one suffering from AIDS or ARC (AIDS related complex), even before the onset of an initial episode of *P. carinii* pneumonia, may avoid or delay suffering from the infection by having administered a prophylactically effective amount of a compound of Formula I or a pharmaceutically acceptable salt thereof. The compound or salt may be administered in the same fashion as in the treatment of patients suffering from *P. carinii* pneumonia.

The present invention also provides new pharmaceutical compositions suitable for intravenous or intramuscular injection. The pharmaceutical compositions comprise a compound of Formula I, or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to compounds of Formula I or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula I, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds of Formula I, or salts thereof, such as aqueous base emulsions. In such an instance, the composition will contain a sufficient amount of pharmaceutically acceptable emulsifying agent to emulsify the desired amount of the compound of Formula I or salt thereof. Particularly useful emulsifying agents include phosphatidyl cholines, and lecithin.

Further, the present invention provides liposomal formulations of the compounds of Formula I and salts thereof. The technology for forming liposomal suspensions is well known in the art. When the compound of Formula I or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula I or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula I or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of Formula I, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of Formula I or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

Examples of compounds exemplary of Formula (I) above include, but are not limited to:

(1) 3,6-diamidinocarbazole dihydrochloride
(2) 3,6-diisopropylamidinocarbazole dihydrochloride
(3) 3,6-bis(2-imidazolinyl)carbazole dihydrochloride
(4) 3,6-bis(2-imidazolinyl)-9-methylcarbazole dihydrochloride
(5) 9-cyclohexylmethyl-3,6-bis(2-imidazolinyl)carbazole dihydrochloride
(6) 3,6-bis[2-(1,4,5,6-tetrahydropyrimidinyl)]-9-methylcarbazole dihydrochloride
(7) 3,6-bis[2-(1,4,5,6-tetrahydropyrimidinyl)]-9-cyclohexylmethylcarbazole dihydrochloride
(8) 3,6-bis[2-imidazolinyl)-2-benzimidazoyl]carbazole tetrahydrochloride
(9) 2,7-diamidinocarbazole dihydrochloride
(10) 2,7-bis(2-imidazolinyl)carbazole dihydrochloride Compounds employed in carrying out the present invention may be prepared in accordance with techniques known to those skilled in the art, particularly in light of the disclosure and examples set forth below.

As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

The salts of the present invention may be prepared, in general, by reacting two equivalents of the pyrimidine base compound with the desired acid, in solution. After the reaction is complete, the salts are crystallized from solution by the addition of an appropriate amount of solvent in which the salt insoluble.

Methods of combating with the compounds of Formula I above are carried out in essentially the same manner as given above, and pharmaceutical formulations of the compounds of Formula I for combating are prepared in essentially the same manner as given above.

Methods of combating *C. neoformans*, *C. parvum*, and *C. albicans* with the compounds of Formula I above are carried out in essentially the same manner as given above, and pharmaceutical formulations of the compounds of Formula I for combating *C. parvum*, *C. neoformans*, and *C. albicans* are prepared in essentially the same manner as given above.

As noted above, the compounds of the present invention may be prepared according to methods known in the art. For example, compounds of Formula I above may be prepared by first preparing an appropriate intermediate, such as 2,4-bis(4-bromophenyl)pyrimidine. The intermediate is prepared by the base promoted condensation of 4-bromobenzamidine and 1-dimethylamino-3-dimethylimmonio-1-(4-bromophenyl)-1-propene, according to the method of R. Wagner, et al., *Chem. Ber.* 104:2975 (1971). The bis-nitrile is readily obtainable by reacting copper(I) cyanide with the thus prepared intermediate in refluxing DMF according to the standard techniques. See, J. Spychala, et al., *European J. Med. Chem.* 29:363 (1994). The bis-nitrile is converted to the imidate ester by the Pinner methodology, according to B. Das, et al., *J. Med. Chem.* 20:1219 (1977). The compounds of Formula I are obtained from the imidate ester according to known techniques. See, Das, et al., supra. Scheme 1 below, outlines the foregoing procedure for preparing compounds of Formula I.

The following examples are provided to illustrate the present invention, and should not be construed as limiting thereon. In these examples, mM means millimolar, mL means milliliters, mm means millimeters, cm means centimeters, °C. means degrees Celsius, g means grams, kg means kilograms, m.p. means melting point, MHz means megahertz, M means molar, h means hours, eV means electron volts, mA means milliamperes, IR means infrared, FTIR means Fourier transform infrared, NMR means nuclear magnetic resonance, FAB means fast atom bombardment, EIMS means electron ionization mass spectrometry, DMF means dimethylformamide, EtOH means ethyl alcohol, DMSO means dimethylsulfoxide, TLC means thin layer chromatography, HPLC means high-pressure liquid chromatography, UV means ultraviolet, sat. means saturated, dec means decomposition point.

In the following examples, uncorrected melting points were measured on a Thomas Hoover capillary melting point apparatus or a Mel-Temp II apparatus. IR spectra were recorded in Nujol mulls or KBr pellets on a Perkin-Elmer 1320 or a Michelson 100 FTIR (Bomen, Inc.) spectrophotometer. $^1$H NMR and $^{13}$C NMR spectra were recorded on Jeol GX-270, Bruker 300, Varian Gemini 300 and XL 400 spectrometers. Chemical shifts are expressed in parts per million relative to tetramethylsilane or sodium 3-(trimethylsilyl)propionate. Anhydrous ethanol was distilled over Mg immediately prior to use. Reaction products were dried over $P_2O_5$ at 77° or 110° C. at 0.2 mm Hg. Unless stated otherwise, reactions were monitored by TLC on silica or by reverse phase HPLC. HPLC chromatograms were recorded on a Hewlett-Packard 1090 chromatograph using a Dupont Zorbax Rx C8 column (4.6 mm×25 cm) and UV detection (230 nm). Mobile phases consisted of mixtures of acetonitrile (5–67.5% v/v) in water containing 10 mM tetramethylammonium chloride, 10 mM sodium heptanesulfonate, and 2.2 mM phosphoric acid. Chromatographic data were recorded and analyzed with a Hewlett-Packard 3396 integrator. Electron impact mass spectra were recorded on a VG 70-SE, a VG 70-SEQ Hybrid, or a JMS 0-100 double-focusing spectrometer. FAB mass spectra were recorded on a VG 70-SEQ Hybrid spectrometer (cesium ion gun, 30 KV). Microanalyses were performed by Atlantic Microlab, Norcross, Ga.

In Examples 1–9, the following compound designations are used throughout.

| Compound # | Name |
| --- | --- |
| 1 | 3,6-diamidinocarbazole dihydrochloride |
| 2 | 3,6-diisopropylamidinocarbazole dihydrochloride |
| 3 | 3,6-bis(2-imidazolinyl)carbazole dihydrochloride |
| 4 | 3,6-bis(2-imidazolinyl)-9-methylcarbazole dihydrochloride |
| 5 | 9-cyclohexylmethyl-3,6-bis(2-imidazolinyl)carbazole dihydrochloride |
| 6 | 3,6-bis[2-(1,4,5,6-tetrahydropyrimidinyl)]-9-methylcarbazole dihydrochloride |
| 7 | 3,6-bis[2-(1,4,5,6-tetrahydropyrimidinyl)]-9-cyclohexylmethylcarbazole dihydrochloride |
| 8 | 3,6-bis[2-imidazolinyl)-2-benzimidazoyl]carbazole tetrahydrochloride |
| 9 | 2,7-diamidinocarbazole dihydrochloride |
| 10 | 2,7-bis(2-imidazolinyl)carbazole dihydrochloride |
| 11 | 3,6-dibromocarbazole |
| 12 | 3,6-dibromo-9-(methyl)carbazole |
| 13 | 3,6-dibromo-9-(cyclohexylmethyl)carbazole |
| 14 | 3,6-dicyanocarbazole |
| 15 | 3,6-dicyano-9-(methyl)carbazole |
| 16 | 3,6-dicyano-9-(cyclohexylmethyl)carbazole |
| 17 | 3,6-diformylcarbazole |
| 18 | 4-(2-imidazolinyl)-1,2-phenylenediamine hydrochloride |
| 19 | 2,5-dibromonitrobenzene |
| 20 | 2,2'-dinitro-4,4'-dibromobiphenyl |
| 21 | 3,8-dibromobenzo[c]cinnoline |
| 22 | 2,2'-diamino-4,4'-dibromobiphenyl |
| 23 | 2,7-dibromocarbazole |
| 24 | 2,3-dicyanocarbazole |

EXAMPLE 1

Synthesis of Novel Compound 1

The syntheses and chemical structures of novel compounds 1–8 are shown in Scheme 1.

A stirred suspension of 2.48 g (11.4 mmol) 3,6-dibromocarbazole in 3.0 mL (51.2 mmol) anhydrous EtOH and 150 mL dry 1,4-dioxane is cooled in an ice-salt bath and is saturated with HCl gas at such a rate that the reaction temperature is maintained below 5° C. The flask is then tightly sealed and the mixture is maintained at room temperature for 21 days, until only a small nitrile band (2200 cm$^{-1}$) is detected by IR analysis. The reaction mixture is purged with N$_2$ gas and diluted with ether (200 mL). The crude diimidate is filtered off under N$_2$ and is immediately suspended in 100 mL anhydrous ethanol. The suspension is diluted with a solution of 3.97 g NH$_3$ (233 mmol) in 100 mL ethanol. The resulting solution is stirred overnight at 35°–50° C. in a tightly stoppered flask. The reaction mixture is filtered through Celite 545 and evaporated. The residue is dissolved in a mixture of hot water and ethanol, filtered, and diluted with acetone to give a precipitate. The precipitate is collected and recrystallized several times from water-acetone to give 0.393 g (10.6%) white crystals. The resulting spectral and analytic data obtained are as follows: m.p.>360° C., $^1$H NMR (300 MHz, DMSO-d$_6$) d12.61(br s, 1H), 9.44 (br s, 4H), 9.16 (br s, 4H), 8.82 (d, J=1.2 Hz, 2H), 7.99 (dd, J=8.6 and 1.2 Hz, 2H), 7.79 (d, J=8.6 Hz, 2H); FAB-MS m/z 252 (MH$^+$ of free base). Anal. ($C_{14}H_{13}N_5 \cdot$2HCl$\cdot H_2O$) C, H, N.
SCHEME 1
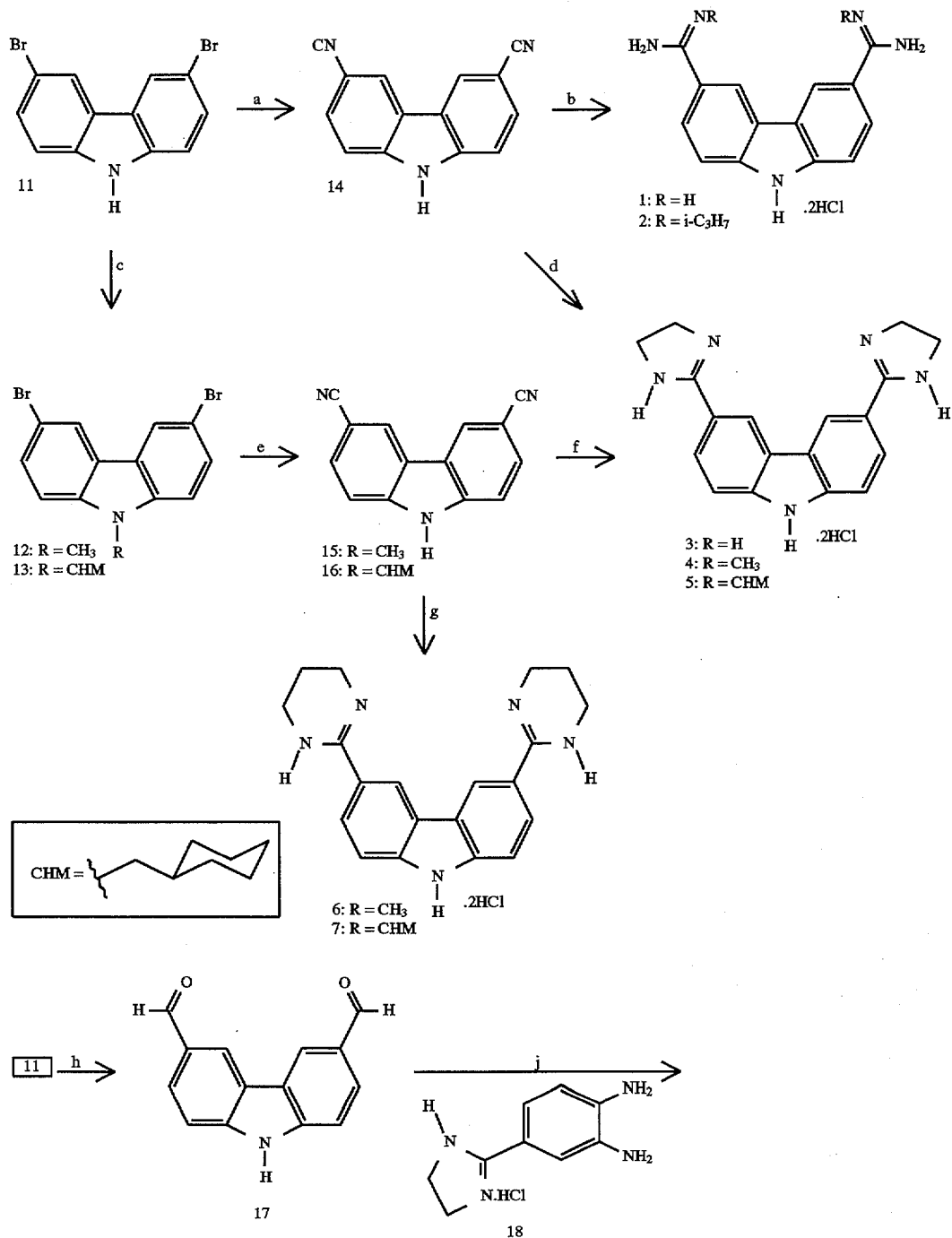

-continued
SCHEME 1

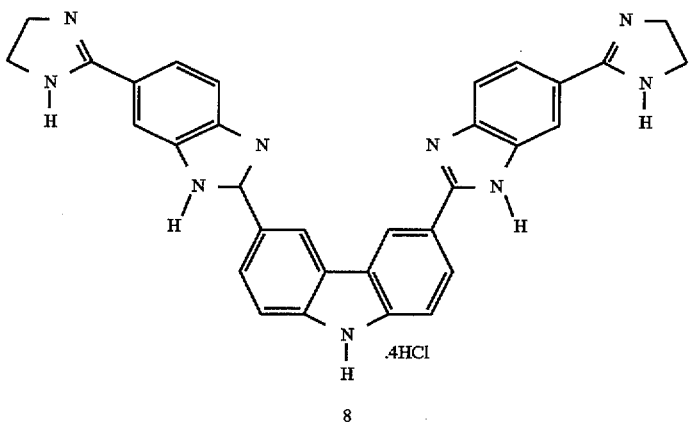

8 a: CuCN, DMF, Δ, 71 h
b: (i)EtOH, HCl, 1,4-dioxane–5–25° C., 17–21 d, (ii)appropriate amine, EtOH, Δ
c: NaH, alkyl halide, DMF, Δ
d: $NH_2(CH_2)_2NH_2 \cdot 2HCl$, 310–320° C., 15 min
e: CuCN, quinoline, Δ, 2 h
f: $NH_2(CH_2)_2NH_2$, $NH_2(CH_2)_2NH_2 \cdot 2HCl$ 300–310° C., 15–30 min
g: $NH_2(CH_2)_3NH_2$, $NH_2(CH_2)_2NH_2 \cdot 2HCl$, 300–310° C., 15–30 min
h: (i)KH, THF, 0° C., (ii)t-BuLi, –78–25° C., (iii)DMF, –78–25° C., (iv)$1MH_3PO_4$;
i: 1,4-benzoquinone, EtOH, Δ, 3.5 h.

EXAMPLE 2

Synthesis of Novel Compound 2

A stirred suspension of 1.645 g (7.59 mmol) 3,6-dicyanocarbazole (compound 14 in FIG. 1) in 3.0 mL (51.4 mmol) anhydrous EtOH and 130 mL dioxane is saturated with HCl gas as described above. The crude diimidate is collected after 17 days and is suspended in 30 mL anhydrous ethanol and 15 mL isopropylamine. The mixture is refluxed under nitrogen for 4.5 hours before more ethanol and isopropylamine (10 mL each) were added. This mixture is refluxed for a total of 20.5 hours. The solvent is evaporated off on a rotary evaporator to give an oily residue, from which a solid is obtained after alkalinization, acidification, and multiple evaporations. The material is recrystallized several times from ethanol-water-acetone to give 0.368 g (11.7%) of a white powder. The resulting spectral and analytic data obtained are as follows: m.p. 317°–318° C.; $^1H$ NMR (400 MHz, DMSO-$d_6$) d 12.59 (br s, 1H), 9.61 (br s, 2H), 9.49 (br s, 2H), 9.11 (br s, 2H), 8.70 (d, J=1.5 Hz, 2H), 7.84 (dd, J=8.6 and 1.5 Hz, 2H), 7.75 (d, J=8.6, 2H), 4.14 (m, 2H); FAB-MS m/z 336 (MH$^+$ of free base). Anal. ($C_{20}H_{25}N_5 \cdot 2HCl$) C, H, N.

EXAMPLE 3

Synthesis of Novel Compound 3

A mixture of 2.01 g (9.27 mmol) 3,6-dicyanocarbazole and 8.36 g (62.9 mmol) ethylenediamine dihydrochloride is pulverized in an agate mortar and heated for 15 minutes at 310°–320° C. in a sand bath. The reaction mixture is nearly completely dissolved in 150 mL boiling water. Insoluble solids were filtered off through Celite 545. The filtrate is concentrated to approximately 25 mL, and the crude product is precipitated out by dilution with 75 mL ethanol. The material is recrystallized several times from mixtures of ethanol and methanol or from mixtures of the same diluted with ether to give 0.310 g (8.9%) pale yellow powder. The resulting spectral and analytic data are as follows:

m.p.>320° C. (dec); $^1H$ NMR (300 MHz, TFA-d)$^d$ 8.44 (s, 2H), 7.93 (d, J=8.6 Hz, 2H), 7.75 (d, J=8.6 Hz, 2H), 4.26 (s, 8H); FAB-MS m/z 304 (MH$^+$ of free base) . Anal. ($C_{18}H_{17}N_5 \cdot 2HCl \cdot 0.5H_2O$) C, H, N.

EXAMPLE 4

Syntheses of Novel Compounds 4–7

The reactions of 6 mmol of the dicyanoaromatic compounds 3,6-dicyano-9-(methyl)carbazole and 3,6-dicyano-9-(cyclohexylmethyl)carbazole (compounds 15 and 16 in FIG. 1) and diaminoalkanes (75 mmol of the base and 80 mmol of the appropriate dihydrochloride) to give cyclic amidines 4–7 were effected in a sand bath at 300°–310° C. (15–30 min). When the reaction is completed by TLC, the unreacted dinitrile is extracted with chloroform or acetone. The product is crystallized from boiling water. The hydrochlorides of the methyl derivatives are more soluble in water than the cyclohexylmethyl amidines. It is preferable to remove unchanged or decomposed material by filtration. The base is precipitated by means of 2M sodium hydroxide solution and the hydrochloride is then prepared using ethanolic hydrogen chloride. The analytical and spectral data are as follows:

Compound (4): m.p.>300° C.; IR (KBr) 3496, 3433, 3103, 2984, 1599, 1491, 1406, 1355, 1317, 1285 cm$^{-1}$; $^1H$ NMR ($D_2O$): d 7.25 (d, 2H, J=8.3 Hz), 7.16 (s, 2H), 6.98 (d, 2H, J=8.3 Hz), 3.95 (s, 8H), 3.30 (s, 3H); $^{13}C$ NMR ($D_2O$) d 166.5, 145.9, 127.9, 123.2, 122.7, 114.1, 112.3, 47.0, 31.8; EIMS (75 eV, 0.3 mA) m/z 317 (M$^+$ of free base). Anal. ($C_{19}H_{19}N_5 \cdot 2HCl \cdot H_2O$) C, H, N.

Compound (5): 2.16 g (71%) of white crystals: m.p.>300° C., IR (KBr) 3096, 2925, 2844, 1603, 1493, 1418, 1361, 1319, 1288, 1251 cm$^{-1}$; $^1H$-NMR (300 MHz, DMSO-$d_6$) d 10.79 (br s, 4H), 8.97 (s, 2H), 8.19 (d, 2H, J=8.8 Hz), 8.09 (d, 2H, J=8.8 Hz), 4.40 (d, 2H, J=7.0 Hz), 4.06 (s, 8H), 1.93 (m, 1H), 1.62 (m, 3H), 1.47 (m, 2H), 1.13 (m, 5H); $^{13}C$ NMR (75 MHz, DMSO-$d_6$) d 166.1, 145.0, 126.7, 122.3, 121.8, 113.3, 111.7, 50.3, 45.4, 38.4, 31.3, 26.6, 26.1; EIMS (75 eV, 0.3 mA) m/z 399 (M$^+$ of free base). Anal. (C$_{25}$H$_{29}$N$_5$•2HCl•2H$_2$O) C, H, N.

Compound (6): m.p.>300° C.; IR (KBr) 3403, 3161, 3020, 1631, 1599, 1493, 1443, 1370, 1316, 1263 cm$^{-1}$; $^1$H-NMR (D$_2$O)d 8.04 (s, 2H), 7.56 (d, 2H, J=8.3 Hz), 7.31 (d, 2H,J=8.3 Hz), 3.72 (br s 8H), 3.52 (s, 3H), 2.24 (br s, 4H); $^{13}$C-NMR (D$_2$O) d 162.0, 146.1, 127.0, 124.0, 121.9, 121.1, 112.7, 42.1, 31.8, 21.0; EIMS (75 eV, 0.3 mA) m/z 345 (M$^+$ of free base). Anal. (C$_{21}$H$_{23}$N$_5$•2HCl•1.75H2O) C, H, N.

Compound (7): 1.89 g (61% of white crystals, m.p.>300° C., IR (KBr) 3146,3016, 2919, 2849, 1631, 1598, 1445, 1375, 1320 cm$^{-1}$; $^1$H NMR (270 MHz, DMSO-d$_6$) d 10.20 (br s, 4H), 8.79 (s, 2H), 7.99 (d, 2H, J=8.8 Hz), 7.85 (d, 2H, J=8.8 Hz), 4.37 (m, 2H), 3.54 (m, 8H), 2.02 (m, 5H), 1.65 (m, 5H), 1.14 (m, 5H); $^{13}$C NMR (67.5 MHz, DMSO-d$_6$) d 159.1, 143.6, 125.8, 121.7, 120.7, 120.5, 110.6, 48.9, 39.2, 37.7, 30.3, 25.8, 25.2, 18.4; EIMS (75 eV, 0.3 mA) m/z 427 (M$^+$ of free base). Anal. (C$_{27}$H$_{33}$N$_5$•2HCl•H$_2$O) C, H, N.

EXAMPLE 5

Synthesis of Novel Compound 8

A mixture of 0.2354 g (1.503 mmol) 3,6-diformylcarbazole (compound 17 in FIG. 1), 0.6380 g (3.000 mmol) 4-(2-imidazolinyl)-1,2-phenylenediamine hydrochloride (compound 18 in FIG. 1), and 0.3882 g (3.5911 mmol) 1,4-benzoquinone in 100 mL ethanol is stirred at reflux for 3.5 hours while exposed to the atmosphere. The reaction mixture is cooled in ice, and the precipitated product (as the dihydrochloride salt) is filtered off. This material is dissolved in 30 mL hot water, and the tetrahydrochloride salt is precipitated out by dilution with 15 mL 4N HCl solution to give 0.498 g (48.9%) of a chartreuse powder with the following spectral and analytic characteristics: m.p.>360° C.; $^1$H NMR (300 MHz, TFA-d) d 9.25 (s, 2H), 8.74 (s, 2H), 8.40 (d, J=8.3 Hz), 8.11 (s, 4H), 7.89 (d, J=8.3 Hz, 2H), 4.32 (s, 8H); FAB-MS m/z 536 (MH$^+$ of free base). Anal. (C$_{32}$H$_{25}$N$_9$•4HCl•3.25H$_2$O) C, H, N.

EXAMPLE 6

Syntheses of Novel Compounds 9 and 10

The preparation and chemical structures of the 2,7-substituted compounds 9 and 10 are shown in Scheme 2. The numbered compounds referred to below refer to their corresponding numbers in FIG. 2. The preparation of compounds 9 and 10 involves first the preparation of 2,7-dibromocarbazole (compound 23). A published three-step synthesis of this compound involves an Ullmann reaction of 2,5-dibromonitrobenzene (compound 19) to give biphenyl compound 20, reduction of the nitro groups of 20 with tin/hydrochloric acid to give diamine compound 22, and a deaminative ring closure catalyzed by Nafion-H to form carbazole compound 23. See Yamato, T. et al., *J. Org. Chem.* 56, 6248–6250 (1991).

Reduction of 20 with stannous chloride dihydrate in refluxing ethanol gave diamine 22 of the highest purity, with a melting point nearly 20° C. higher than the literature value, and in a yield of 63%, only slightly less than that obtained from the tin/HCl reduction in the literature. See Yamato, et al., supra. 3,8-Dibromobenzo[c]cinnoline (compound 21) is isolated as a minor product by either the stannous chloride or tin/HCl reduction (yields of 17 and 3%, respectively). The reduction of 20 using 5% rhydrazine hydraten and hydrazine hydrate in refluxing ethanol gave decreased amounts of 22 and increased amounts of 21. This compound is also prepared by the reduction of 20 with lithium aluminum hydride. Benzo[c]cinnolines such as 21 are also prepared by the reduction of 2,2'-dinitrobiphenyls with sodium sulfide (see Corbett, J. F. et al., *J. Chem. Soc.* 5029–5037 (1961)), hydrazine-Raney Nickel (see Barton, J. W. and D. J. Lapham, *J.C.S. Perkin Trans.* I 1503–1505 (1979)), hydrazine with a catalyst prepared by reduction of nickel nitrate with zinc (see Yun, T. H. et al., *J. Chem. Res. Synop.* 10, 336–337 (1992)), or electrochemically using titanium oxysulfate (see Martre, A.-M., et al., *Can J. Chem.* 71, 1136–1146 (1993)).

The Nafion-catalyzed cyclization reaction of 21 to 23 is achieved using 85% phosphoric acid at 200° C. The melting point of product 23 is about 25° C. higher than the literature value. Cf. Yamoto, et al., supra. The reaction of dibromide 23 with copper (I) cyanide in refluxing DMF to give dinitrile compound 24 is complete after 9 hours (as compared to 70 hours for the 3,6-regioisomer). Dinitrile 24 is much more reactive to Pinner synthesis conditions than regioisomer 14; the formation of the diimidate derivative of 24 is complete after 5 days. Reaction of the diimidate derivative of 24 with ammonia give novel diamidine compound 9. The neat fusion of 24 with ethylenediamine dihydrochloride gave diimidazoline 10.

To obtain compound 9, a stirred suspension of 1.68 g (7.74 mmol) 2,7-dicyanocarbazole (compound 22 in FIG. 2) in 3.0 mL (51.12 mmol) anhydrous ethanol and 100 mL dry 1,4-dioxane is saturated with HCl gas as described in the synthesis of compound 1, above. The crude diimidate is collected after 5 days reaction time. A suspension of the diimidate in 15 mL anhydrous ethanol is diluted with a solution of 7.26 g ammonia in 85 mL ethanol and stirred overnight at 40° C. in a stoppered flask. The cooled reaction mixture is poured into 125 mL cold ether, and the resulting precipitate is filtered off. The material is recrystallized once from water-ethanol-acetone and four times from water acetone to give 0.4820 g (19.2%) of a light yellow powder, with the following spectral and analytical characteristics: m.p.>360° C. (dec); $^1$H NMR (400 MHz, DMSO-d$_6$) d 12.53 (s, 1H), 9.52 (s, 4H), 9.27 (s, 4H), 8.49 (d, J=8.8 Hz, 2H), 8.08 (s, 2H), 7.65 (d, J=8.8 Hz, 2H); FAB-MS m/z 252 (MH$^+$ of free base). Anal. (C$_{14}$H$_{13}$N$_5$•2HCl) C, H, N.

To obtain compound 10, a mixture of 0.9886 g (4.5511 mmol) 2,7-dicyanocarbazole (compound 22 in FIG. 2) and 3.00 g (22.6 mmol) ethylenediamine dihydrochloride is pulverized in an agate mortar and at heated at 320° C. for 30 min. After being allowed to cool, the reaction mixture is dissolved in 100 mL hot water and filtered through Celite 545. The filtrate is concentrated by boiling to approximately 5 mL, and a solid precipitated from the solution upon cooling. The precipitate is collected and dissolved in methanol, and the solution is filtered through Norit-A (3 mm layer). A yellow solid is precipitated from the concentrated filtrate by dilution with ether, then recrystallized from hot water-EtOH (20 mL each) to give 0.3878 g (22.6%) of yellow microcrystals with the following characteristics: m.p.>360° C.; $^1$H NMR (300 MHz, CF$_3$COOH-d$_6$) d 8.36 (d, J=8.2 Hz, 2H), 8.19 (s, 2H), 7.67 (d, J=8.2 Hz, 2H), 4.27 (s, 8H); FAB-MS m/z 304 (MH$^+$ of free base). Anal. (C$_{18}$H$_{17}$N$_5$•2HCl•0.9H$_2$O) C, H, N.

SCHEME 2

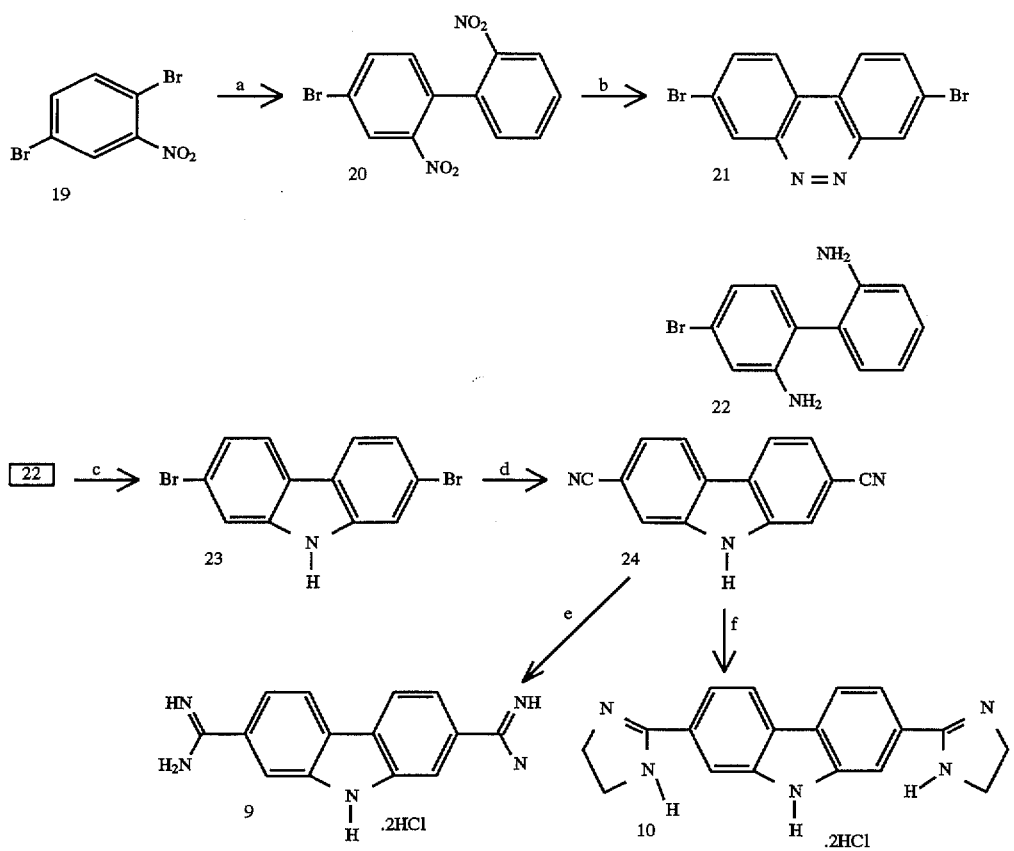

a: Cu, DMF, 120° C., 2 h;
b: Sn, conc. HCl, EtOH, Δ, 1 h;
c: 85% H₃PO₄, 200° C., 44 h;
d: CuCN, DMF, Δ, 9 h;
e: (i)EtOH, HCl, 1,4-dioxane -5-25° C., 5 d, (ii)EtOH/NH₃, 40° C., 16 h;
f: NH₂(CH₂)₂NH₂.2HCl, 310-320° C., 30 min.

EXAMPLE 7
Activity of Novel Compounds Against Pneumocystis carinii

The activity of the compounds against *P. carinii* was carried out according to an established method. See Tidwell, R. R., et al., *J. Med. Chem.* 33, 1252-1257 (1990); Jones, S. K., et al., *Antimicrob. Agents Chemother.* 34, 1026-1030 (1990); Tidwell, R. R., et al., *Antimicrob. Agents Chemother.* 37, 1713-1716 (1993). The induction and treatment of *P. carinii* pneumonia (PCP) was carried out with only minor alterations to published methods. See Frenkel, J. K. et al., *Lab. Invest.* 15, 1559 (1966); Hughes, W. T. et al., *Antimicrob. Agents Chemother.* 5, 289 (1974). Briefly, male Sprague-Dawley rats (barrier raised, not certified virus-free) weighing 150-200 g each, were obtained (Hilltop Laboratories, Scottsdale, Pa). Immediately upon arrival, the animals were caged individually and begun on a low protein (8%) diet and on drinking water containing tetracycline (0.5 mg/mL) and dexamethasone (1.0 μ/mL). This regimen was continued for eight weeks. At the beginning of the seventh week, animals were divided into groups of 8 or more, and the test compounds were administered for 14 days by single daily IV injection. Generally, the daily dose was 5 mg/kg of body weight and was dissolved in 0.4 mL of saline. Saline- and pentamidine-treated groups were included as controls.

Animals were sacrificed at the end of the eighth week by chloroform inhalation. The right lung was inflated in situ with 10% formalin and fixed for histological examination. The lung tissue was sectioned in the long axis and exposed to the GMS stain, which selectively identified the walls of the *P. carinii* cysts.

The left lung was weighed, ground through a No. 60 wire mesh screen, and suspended 1:10 (wt/vol) in 10 mM β-mercaptoethanol-Hanks' balanced salts solution (HBSS) without cations. Slides were prepared by spotting 5 μL of lung homogenate diluted 1:10 in HBSS with β-mercaptoethanol and allowed to air dry. The slides were stained with cresyl violet, and the cysts were counted by a blinded protocol. The number of cysts per gram of original lung tissue was calculated, and the groups were reported as the percentages of saline-treated controls.

As seen in Table 1, the majority of the novel compounds tested showed excellent activity in the rat model of *P. carinii* pneumonia. Anti-*P. carinii* activity is measured by the reduction in the number of cysts per gram of lung tissue for treated animals as compared to untreated controls. The anti-*P. carinii* value for each compound is expressed as the percent of cysts in the treatment group as compared to the control group. Only compounds 5, 7, and 8 failed to exhibit anti-*P. carinii* significantly more potent than the control drug, pentamidine. Compound 3 showed over a log greater activity when compared to pentamidine. It should be noted that compound 3 was tested at one half the dose of pentamidine as were all of the carbazoles.

As a series, the carbazoles tested contain some of the most potent anti-*P. carinii* agents tested in several years of testing drugs against *P. carinii* pneumonia. Cf. Jones, S. K. et al., *Antimicrob. Agents Chemother.* 34, 1026–1030 (1990); Tidwell, R. R. et al., *Pneumocystis carinii*, (Walzer, P., ed.; Marcel Decker: New York) pp. 561–583 (1993); Tidwell, R. R. et al., *J. Protozool.* 36, 74S–76S (1989); Donkor, I. O., et al., *J. Med. Chem.* 37, 4554–4557 (1994); Tidwell, R. R. et al., *Antimicrob. Agents Chemother.* 37, 1713–1716 (1993). Compound 3 gave the lowest percent of cysts of any compound previously tested.

mented and is a considered a standard method for determining DNA binding strength. See Cory, M.. et al., *J. Med. Chem.* 25, 431–438 (1992). In brief, a UV-visible light spectrophotometer with a cuvette changer was interfaced to a microcomputer that recorded the cuvette temperature and DNA-absorbance data at 259 nm as the sample was heated at a rate of 18° C./h. Calf thymus DNA was used at an initial absorbance of 0.3 $A_{259}$. The midpoint of each denaturation curve was determined after graphic selection on the computer of the starting and ending absorbance temperature for each curve of each experiment. DNA or DNA bound to experimental compound was run in each experiment and the $\Delta T_m$s were determined from the polynucleotide $T_m$ for that experiment. The greater the change in melting point, the more potent the DNA binding of the molecules. The data

TABLE 1

DNA Binding and Activity Against *Pneumocystis carinii* Pneumonia (PCP) by Novel Carbazoles.

| | in vivo activity against PCP | | | DNA binding |
|---|---|---|---|---|
| compounds | dose mg/kg (iv) | toxicity | cysts/g lung % control[a] | calf thymus $\Delta T_m$(°C.) |
| saline | — | 0 | 100.00 ± 15.36 | |
| pentamidine | 10.0 | ++ | 1.84 ± 0.82[b] | 10.7 |

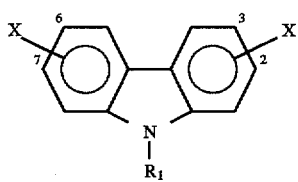

| cmpd no. | X | position X | $R_1$ | | | | |
|---|---|---|---|---|---|---|---|
| 1 | Am | 3,6 | H | 5.0 | 0 | 0.80 ± 0.36[b] | 17.2 |
| 2 | IsoAm | 3,6 | H | 5.0 | 0 | 0.11 ± 0.08[b] | 9.6 |
| 3 | Im | 3,6 | H | 5.0 | 0 | 0.06 ± 0.02[b] | 19.5 |
| 4 | Im | 3,6 | $CH_3$ | 5.0 | +++ | 0.17 ± 0.11[b] | 24.0 |
| 5 | Im | 3,6 | CHM | 5.0 | 0 | 35.78 ± 4.87[c] | 16.8 |
| 6 | THP | 3,6 | $CH_3$ | 5.0 | + | 0.14 ± 0.05[b] | 13.6 |
| 7 | THP | 3,6 | CHM | 5.0 | + | 4.10 ± 1.59[b] | 7.3 |
| 8 | Bzlm | 3,6 | H | 5.0 | 0 | 61.91 ± 14.46[d] | 22.2 |
| 9 | Am | 2,7 | H | 5.0 | 0 | 0.17 ± 0.06[b] | 19.0 |
| 10 | Im | 2,7 | H | 5.0 | 0 | 0.50 ± 0.33[b] | 18.6 |

[a]Values are the means ± SEM.
[b]$p < 0.001$ vs saline.
[c]$p < 0.01$ vs saline.
[d]$p < 0.05$ vs pentamidine.

EXAMPLE 8

Binding of Novel Compounds to DNA

DNA binding potency was determined for each of the compounds because previous work had determined that the binding of dicationic molecules to DNA is a prerequisite for their antimicrobial activity. See e.g., Tidwell, R. R., et al., *Antimicrob. Agents Chemother.* 37, 1713–1716 (1993); Bell, C. A., et al., *Antimicrob. Agents Chemother.* 35, 1099–1107 (1991). The DNA binding of the novel compounds was determined by the change in melting of the DNA bound to the experimental compounds. The method is well documented in Table 1 represent the average of at least two determinations of $\Delta T_m$.

Table 1 illustrates that the strength of DNA binding does not correlate with anti-*P. carinii* potency. However, it has been previously reported that while strong DNA binding is a prerequisite for antimicrobial activity, the strength of DNA binding does not necessarily reflect the degree of antimicrobial action. See Cory, M. et al., *J. Med. Chem.* 25, 431–438 (1992); Fairley, T. et al., *J. Med. Chem.* 36, 1846–1753 (1993).

Interestingly, compound 8 showed only moderate activity in the *P. carinii* animal model but was highly potent as a DNA binding agent. The inferior anti-*P. carinii* activity could be attributed to the poor solubility and distribution of this larger molecule.

EXAMPLE 9

Activity of Compound 9 against Other Opportunistic Pathogens

The activity of compound 9 against three additional AIDS-associated opportunistic pathogens is shown in Table 2. Besides the potency shown by this compound against *P. carinii* infection in the rat model, the compound was also effective in a neonatal mouse model of *Cryptosporidium parvum* infection. This model has been described in detail in previous reports. See Blagburn, B. L.; et al., *Antimicrob. Agents Chemother.* 35, 1520–1523 (1991). The compound's activity against *C. parvum* is measured by a reduction in the number of oocysts detected in the bowel of treated mice compared to untreated controls.

Compound 9 was also highly active in vitro against *Cryptococcus neoformans* and *Candida albumins*. Activity of the compound was assessed using a standard in vitro fungal cell growth inhibition assay (the broth dilution antifungal susceptibility testing of yeast, proposed standard document M27-P, validated by the National Committee for Clinical Laboratory Standards, 1992). Briefly, this broth dilution procedure uses PMI media, and an inoculum of 104 control tubes with media alone. After the minimal inhibitor concentration was determined by the above procedure, tubes with no visible growth were subcultured to determine the minimum fungicidal concentration by using criteria of less than 0.01% survival of original inoculum. Two organisms were tested: (1) H99, a clinical isolate of *C. neoformans* which is fully susceptible to azoles and polyenes in vitro and in vivo; and (2) A39, a clinical isolate of *C. albicans* which is fully susceptible to azoles and polyenes.

The MFC's (minimum fungicidal concentration) for compound 9 against these two important AIDS-associated fungal infections are shown in Table 2.

The data in Table 2 illustrates the potential for this series of compounds to have broad spectrum antimicrobial activity.

TABLE 2

Broad spectrum of activity by Compound 9.

|   | Dose | Route | Efficacy |
|---|---|---|---|
| *P. carinii* | 15.4 µmol/kg | iv | 0.19% control |
| *C. parvum* | 58.6 µmol/kg | oral | 0.89% control |
|   | 29.3 µmol/kg | oral | 0.30% control |
|   | 14.6 µmol/kg | oral | 6.1% control |
| *C. neoformans* |   | in vitro | MIC = 6.25 µg/mL |
|   |   |   | MFC = 50.0 µg/mL |
| *C. albicans* |   | in vitro | MIC = 0.78 µg/mL |
|   |   |   | MFC = 1.56 µg/mL |

MFC = minimal fungicidal dose. MIC = minimal inhibitory concentration. MIC and MFC determinations for *C. neoformans* and *C. albicans*. MIC determinations were performed according to the NCCLS proposed standard M27-P (1992). The minimum fungicidal concentrations (MFCs) were determined following the method of McGinnis.

That which is claimed is:

1. A method of treating *Pneumocystis carinii* pneumonia in a subject in need of such treatment, comprising administering to said subject a compound of Formula I:

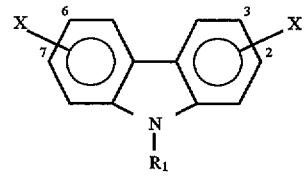

wherein:

x is located in the para or meta positions and is loweralkyl, loweralkoxy, alkoxyalkyl, hydroxyalkyl, aminoalkyl, alkylaminoalkyl, cycloalkyl, aryl, alkylaryl, halogen, or

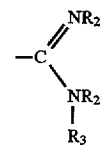

wherein:

each $R_2$ is independently selected from the group consisting of H, loweralkyl, alkoxyalkyl, hydroxyalkyl, aminoalkyl, alkylaminoalkyl, cycloalkyl, aryl, or alkylaryl or two $R_2$ groups together represent $C_2$–$C_{10}$ alkylene, or two $R_2$ groups together represent

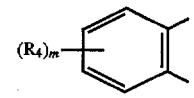

wherein
m is from 1–3 and $R_4$ is H,

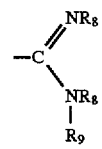

or —$CONHR_5NR_6R_7$, wherein $R_5$ is loweralkyl, $R_6$ and $R_7$ are each independently selected from the group consisting of H and lower alkyl; each $R_8$ is independently selected from the group consisting of H, loweralkyl, alkoxyalkyl, hydroxyalkyl, aminoalkyl, alkylaminoalkyl, cycloalkyl, aryl, or alkylaryl, or two $R_8$ groups together represent $C_2$–$C_{10}$ alkylene; $R_9$ is H, hydroxy, loweralkyl, alkoxyalkyl, hydroxyalkyl, aminoalkyl, alkylaminoalkyl, cycloalkyl, aryl, or alkylaryl;

$R_3$ is H, hydroxy, loweralkyl, alkoxyalkyl, hydroxyalkyl, aminoalkyl, alkylaminoalkyl, cycloalkyl, aryl, or alkylaryl; $R_1$ is H, loweralkyl, alkoxyalkyl, hydroxyalkyl, aminoalkyl, alkylaminoalkyl, cycloalkyl, aryl, alkylaryl, or halogen;

or a pharmaceutically acceptable salt thereof, in an amount effective to treat *Pneumocystis carinii* pneumonia.

2. The method according to claim 1, wherein said subject is afflicted with *Pneumocystis carinii* pneumonia.

3. The method according to claim 1, wherein said subject is at risk of developing *Pneumocystis carinii* pneumonia and said compound is administered in a prophylactically effective amount.

4. The method according to claim 1, wherein X is in the para position.

5. The method according to claim 1, wherein X is in the meta position.

6. The method according to claim 1, wherein X is

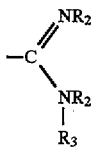

and wherein said compound of Formula (I) is selected from the group consisting of compounds wherein (a) $R_1$ is H, each $R_2$ is H, and $R_3$ is H;

(b) $R_1$ is H, one $R_2$ is loweralkyl, one $R_2$ is H, and $R_3$ is H;

(c) $R_1$ is H, each $R_2$ is loweralkyl, and $R_3$ is H;

(d) $R_1$ is H, two $R_2$ groups together represent $C_2$ alkylene, and $R_3$ is H;

(e) $R_1$ is H, two $R_2$ groups together represent $C_3$ alkylene, and $R_3$ is H;

(f) $R_1$ is loweralkyl, each $R_2$ is H, and $R_3$ is H;

(g) $R_1$ is loweralkyl, one $R_2$ is loweralkyl, one $R_2$ is H, and $R_3$ is H;

(h) $R_1$ is loweralkyl, each $R_2$ is loweralkyl, and $R_3$ is H;

(i) $R_1$ is loweralkyl, two $R_2$ groups together represent $C_2$ alkylene, and $R_3$ is H;

(j) $R_1$ is loweralkyl, two $R_2$ groups together represent $C_3$ alkylene, and $R_3$ is H;

(k) $R_1$ is cycloalkyl, each $R_2$ is H, and $R_3$ is H;

(l) $R_1$ is cycloalkyl, one $R_2$ is loweralkyl, one $R_2$ is H, and $R_3$ is H;

(m) $R_1$ is cycloalkyl, each $R_2$ is loweralkyl, and $R_3$ is H;

(n) $R_1$ is cycloalkyl, two $R_2$ groups together represent $C_2$ alkylene, and $R_3$ is H;

(o) $R_1$ is cycloalkyl, two $R_2$ groups together represent $C_3$ alkylene, and $R_3$ is H.

7. The method according to claim 1, wherein said compound of Formula I is selected from the group consisting of 3,6-diamidinocarbazole dihydrochloride, 3,6-diisopropylamidinocarbazole dihydrochloride, 3,6-bis(2-imidazolinyl)carbazole dihydrochloride, 3,6-bis(2-imidazolinyl)-9-methylcarbazole dihydrochloride, 9-cyclohexylmethyl-3,6-bis(2-imidazolinyl)carbazole dihydrochloride, 3,6-bis[2-(1,4,5,6-tetrahydropyrimidinyl)]-9-methylcarbazole dihydrochloride, 3,6-bis[2-(1,4,5,6-tetrahydropyrimidinyl)]-9-cyclohexylmethylcarbazole dihydrochloride, 3,6-bis[2-imidazolinyl)-2-benzimidazoyl]carbazole tetrahydrochloride, 2,7-diamidinocarbazole dihydrochloride, and 2,7-bis(2-imidazolinyl)carbazole dihydrochloride.

* * * * *